(12) United States Patent
Dahan et al.

(10) Patent No.: US 8,563,514 B2
(45) Date of Patent: Oct. 22, 2013

(54) PEPTIDES AND PHARMACEUTICAL COMPOSITIONS FOR TREATING CONNECTIVE TISSUE

(75) Inventors: Mazal Dahan, Mazkeret Batia (IL); Raphael Gorodetsky, Jerusalem (IL)

(73) Assignee: Metamorefix, Rehovot, IL (US)

( * ) Notice: Subject to any disclaimer, the term of this patent is extended or adjusted under 35 U.S.C. 154(b) by 458 days.

(21) Appl. No.: 12/733,137

(22) PCT Filed: Aug. 14, 2008

(86) PCT No.: PCT/IL2008/001121
§ 371 (c)(1),
(2), (4) Date: Apr. 30, 2010

(87) PCT Pub. No.: WO2009/022340
PCT Pub. Date: Feb. 19, 2009

(65) Prior Publication Data
US 2010/0210544 A1   Aug. 19, 2010

Related U.S. Application Data

(60) Provisional application No. 60/935,490, filed on Aug. 15, 2007, provisional application No. 61/006,501, filed on Jan. 16, 2008.

(51) Int. Cl.

| | |
|---|---|
| *A61K 38/00* | (2006.01) |
| *A61K 38/16* | (2006.01) |
| *A61K 38/10* | (2006.01) |
| *A61K 47/00* | (2006.01) |
| *A61K 47/48* | (2006.01) |
| *A61K 38/17* | (2006.01) |
| *A61K 38/39* | (2006.01) |
| *A61P 17/00* | (2006.01) |
| *A61P 43/00* | (2006.01) |
| *C07K 14/705* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *C07K 14/47* | (2006.01) |
| *C07K 14/78* | (2006.01) |

(52) U.S. Cl.
USPC ....... 514/18.6; 514/18.8; 514/19.1; 514/21.3; 514/21.4; 514/1.1; 514/1.2; 514/16.5; 530/300; 530/324; 530/326

(58) Field of Classification Search
None
See application file for complete search history.

(56) References Cited

U.S. PATENT DOCUMENTS

| | | | |
|---|---|---|---|
| 6,831,172 B1 | 12/2004 | Barbucci et al. | |
| 6,969,531 B2 | 11/2005 | Dehazya et al. | |
| 7,163,701 B2 | 1/2007 | Cleland et al. | |
| 2005/0177118 A1 | 8/2005 | Hoganson et al. | |
| 2005/0282747 A1* | 12/2005 | Clark et al. | 514/12 |
| 2011/0275573 A1* | 11/2011 | Dahan et al. | 514/17.1 |
| 2012/0058956 A1* | 3/2012 | Dahan et al. | 514/21.3 |

FOREIGN PATENT DOCUMENTS

| | | |
|---|---|---|
| CA | 2 551 121 A1 | 7/2005 |
| WO | WO 9961041 A1 * | 12/1999 |
| WO | 01/53324 A2 | 7/2001 |
| WO | 03/076578 A2 | 9/2003 |
| WO | WO 03076578 A2 * | 9/2003 |

OTHER PUBLICATIONS

Luo et al., "Cross-linked hyaluronic acid hydrogel films: new biomaterials for drug delivery," J. Contr. Rel. 69:169-184 (2000).*
GenBank Accession No. AAB50706, *Homo sapiens* ficolin (1997).*
Blast sequence alignment results between GenBank Accession No. AAB50706 and the "peptide-71" sequence in WO 99/61041 A1.*
The International Search Report for International Application No. PCT/IL2008/001121, mailed Jan. 5, 2009, three pages.
Database NCBI [Online] ficolin; XP002507812; Database accession No. AAB50706; abstract; one page, (1997).
Database NCBI[Online] fibronectin; XP002507813; Database accession No. AAD00019; abstract; one page; (1999).
Harumiya, et al., "Characterization of Ficolins as Novel Elastin-Binding Proteins and Molecular Cloning of Human Ficolin-1", J. Biochem., vol. 120, pp. 745-751, (1996).
Motokawa, et al., "Selectively crosslinked hyaluronic acid hydrogels for sustained release formulation of erythropoietin", J Biomed Mater Res, vol. 78A, pp. 459-465, (2006).
Prestwich, et al., "Controlled chemical modification of hyaluronic acid: synthesis, applications, and biodegradation of hydrazide derivatives", Journal of Controlled Release, vol. 53, pp. 93-103, (1998).
Luo, et al., "Cross-linked hyaluronic acid hydrogel films: new biomaterials for drug delivery", Journal of Controlled Release, vol. 69, pp. 169-184, (2000).

(Continued)

*Primary Examiner* — Marcela M Cordero Garcia
*Assistant Examiner* — Thea D'Ambrosio
(74) *Attorney, Agent, or Firm* — Dennis A. Bennett

(57) ABSTRACT

Provided is a pharmaceutical composition for sequestering cells in connective tissue. The composition includes a biocompatible scaffolding to which one or more peptides or proteins are linked. The peptides or proteins have an amino acid sequence that is a subsequence of human ficolin and are capable of binding the cells to be sequestered. The pharmaceutical composition can be used in the treatment of connective tissue, and can be used as a dermal filler.

**16 Claims, 13

(56) References Cited

OTHER PUBLICATIONS

Hahn, et al., "Sustained release formulation of erythropoietin using hyaluronic acid hydrogels crosslinked by Michael addition", International Journal of Pharmaceutics, vol. 322, pp. 44-51, (2006).

Collins, et al., "Comparison of the Effectiveness of Four Different Crosslinking Agents with Hyaluronic Acid Hydrogel Films for Tissue-Culture Applications", J Appl Polym Sci, vol. 104, pp. 3183-3191, (2007).

Kurisawa, et al., "Injectable biodegradable hydrogels composed of hyaluronic acid-tyramine conjugates for drug delivery and tissue engineering", Chem. Commun., pp. 4312-4314, (2005).

Park, et al., "Photopolymerized hyaluronic acid-based hydrogels and interpenetrating networks", Biomaterials, vol. 24, pp. 893-900, (2003).

Himeda, et al., "Effectiveness of a Novel Hyaluronic-Acid Gel Film in the Rat Model", J Gynecol Surg, vol. 21, No. 2, pp. 55-63, (2005).

Glass, et al., "Characterization of a hyaluronic acid-Arg—Gly—Asp peptide cell attachment matrix", Biomaterials, vol. 17, No. 11, pp. 1101-1108, (1996).

Leach, et al., "Development of photocrosslinkable hyaluronic acid-polyethylene glycol-peptide composite hydrogels for soft tissue engineering", J Biomed Mater Res, vol. 70A, pp. 74-82, (2004).

Lu, et al., "Human ficolin: cDNA cloning, demonstration of peripheral blood leucocytes as the major site of synthesis and assignment of the gene to chromosome 9", Biochem. J., vol. 313, pp. 473-478, (1996).

Blast sequence alignment results between GenBank Accession No. AAB50706 and the "peptide-71" sequence in WO 99/61041 A1, (conducted Sep. 2012).

\* cited by examiner

SEQUENCE LISTING

<160> NUMBER OF SEQ ID NOS: 10

<210> SEQ ID NO 1
<211> LENGTH: 16
<212> TYPE: PRT
<213> ORGANISM: Homo sapiens

<400> SEQUENCE: 1

Lys Gly Tyr Asn Tyr Ser Tyr Lys Ser Glu Met Lys Val Arg Pro Ala
1               5                   10                  15

<210> SEQ ID NO 2
<211> LENGTH: 19
<212> TYPE: PRT
<213> ORGANISM: Homo sapiens

<400> SEQUENCE: 2

-continued

Gly Gly Trp Thr Val Phe Gln Arg Arg Val Asp Gly Ser Val Asp Phe
1               5                   10                  15

Tyr Arg Lys

<210> SEQ ID NO 3
<211> LENGTH: 27
<212> TYPE: PRT
<213> ORGANISM: Homo sapiens

<400> SEQUENCE: 3

Lys Gly Tyr Asn Tyr Ser Tyr Lys Val Ser Glu Met Lys Phe Gln Arg
1               5                   10                  15

Arg Val Asp Gly Ser Val Asp Phe Tyr Arg Lys
            20                  25

<210> SEQ ID NO 4
<211> LENGTH: 18
<212> TYPE: PRT
<213> ORGANISM: Homo sapiens

<400> SEQUENCE: 4

Lys Gly Tyr Lys Tyr Ser Tyr Lys Val Ser Glu Met Lys Val Arg Pro
1               5                   10                  15

Ala Lys

<210> SEQ ID NO 5
<211> LENGTH: 19
<212> TYPE: PRT
<213> ORGANISM: Homo sapiens

<400> SEQUENCE: 5

Gly Gly Trp Thr Val Phe Gln Arg Arg Met Asp Gly Ser Val Asp Phe
1               5                   10                  15

Tyr Arg Lys

<210> SEQ ID NO 6
<211> LENGTH: 27
<212> TYPE: PRT
<213> ORGANISM: Homo sapiens

<400> SEQUENCE: 6

Lys Gly Tyr Lys Tyr Ser Tyr Lys Gly Gly Trp Thr Val Phe Gln Arg
1               5                   10                  15

Arg Met Asp Gly Ser Val Asp Phe Tyr Arg Lys
            20                  25

<210> SEQ ID NO 7
<211> LENGTH: 27
<212> TYPE: PRT
<213> ORGANISM: Homo sapiens

<400> SEQUENCE: 7

Lys Gly Tyr Lys Tyr Ser Tyr Lys Val Ser Glu Met Lys Phe Gln Arg
1               5                   10                  15

Arg Met Asp Gly Ser Val Asp Phe Tyr Arg Lys
            20                  25

<210> SEQ ID NO 8
<211> LENGTH: 26
<212> TYPE: PRT
<213> ORGANISM: Homo sapiens

<400> SEQUENCE: 8

```
Lys Gly Tyr Lys Tyr Ser Tyr Lys Gly Gly Trp Thr Val Phe Gln Arg
1               5                   10                  15

Arg Met Asp Gly Ser Val Asp Phe Tyr Arg
            20                  25

<210> SEQ ID NO 9
<211> LENGTH: 27
<212> TYPE: PRT
<213> ORGANISM: Homo sapiens

<400> SEQUENCE: 9

Lys Thr Arg Trp Tyr Ser Met Lys Lys Thr Thr Met Lys Val Phe Gln
1               5                   10                  15

Lys Arg Leu Val Gly Ser Val Asp Phe Lys Lys
            20                  25

<210> SEQ ID NO 10
<211> LENGTH: 19
<212> TYPE: PRT
<213> ORGANISM: Homo sapiens

<400> SEQUENCE: 10

Lys Thr Arg Trp Tyr Ser Met Lys Lys Thr Thr Met Lys Ile Ile Pro
1               5                   10                  15

Phe Asn Arg
```

PEPTIDES AND PHARMACEUTICAL COMPOSITIONS FOR TREATING CONNECTIVE TISSUE

This is a National Phase Application filed under 35 U.S.C. 371 as a national stage of PCT/IL2008/001121, filed Aug. 14, 2008, an application claiming the benefit under 35 USC 119 (e) U.S. Provisional Application No. 60/935,490, filed Aug. 15, 2007, and U.S. Provisional Application No. 61/006,501, filed Jan. 16, 2008, the content of each of which is hereby incorporated by reference in its entirety.

FIELD OF THE INVENTION

This invention relates to pharmaceutical compositions for treating connective tissue.

The Sequence Listing submitted in text format (.txt) on Apr. 30, 2010, named "12733137_Sequence_Listing.txt, (created on Apr. 21, 2010, 3 KB), is incorporated herein by reference.

BACKGROUND OF THE INVENTION

The following prior art publications are considered as relevant for an understanding of the invention. The publications are referred to herein by their number in the following list:
1. "Selectively cross linked Hyaluronic acid hydrogels for sustained release formulation for Erythropoietyn", K. Motokawa, S. K. Hahn, T. Nakamura, H. Miyamoto, T. Shimoboji, J. of Biomed. Mat. Res., part A, DOI 10.1002, pp 459-465, 2006.
2. Controlled chemical modification of Hyaluronic acid: Synthesis, applications and biodegradations of hydrazide derivatives", G. D. Prestwich, D. M. Marecak, J. F. Marecek, K. P. Vercruysse, M. R. Ziebell, J. Cont. Rel., vol. 53, pp 93-103, 1998.
3. "Cross-linked hyaluronic acid hydrogel films: New biomaterials for drug delivery", Y. Lou, K. R. Kirker, G. D. Prestwich, J. Cont. Rel., vol. 69, pp 169-184, 2000.
4. "Sustained release formulation of erythropoietin using hyaluronic acid hydrogels cross-linked by Michael addition", S. K. Hahn, E. J. Oh, H. Miyamoto, T. Shimobouji, Int. J. of Pharm. 322, pp 44-51, 2006.
5. "Comparison of the effectiveness of four different crosslinking agents with Hyaluronic acid hydrogel films for tissue culture application", M. N. Collins, C. Birkinshaw, J. of Appl. Pol. Sci., Vol. 104, pp 3183-3191, 2007.
6. U.S. Pat. No. 6,831,172.
7. "Injectable biodegradable hydrogels composed of hyaluronic acid-tyramine conjugates for delivery and tissue engineering", M. Kurisawa, J. E. Chung, Y. Y. Yang, S. J. Gao, H. Uyama, Chem. Commun., 2005, pp 4312-4314.
8. "Photopolymerized hyaluronic acid-based hydrogels and interpenetrating networks", Y. D. Park, N. Tirelli, J. A. Hubbell, Biomat. 24, pp 893-900, 2003.
9. "Controlled chemical modification of hyaluronic acid: synthesis, applications, and biodegradation of hydrazide derivatives", G. D. Prestwich, D. M. Marecak, J. F. Marecek, K. P. Vorcruysse, M. R. Ziebell, J. Con. Rel., 53, pp 93-103, 1998.
10. US patent application #20050177118
11. "Effectiveness of a new novel Hyaluronic-acid gel film in the rat model", Y. Himeda, H. Kaneko, T. Umeda, Y. Miyata, T. Miyoshi, J. of Gynecologic Surgery, vol 21(2), pp 55-63, 2005.
12. "Characterization of Hyaluronic acid-Arg-Gly-Asp peptide cell attachment matrix", J. R. Glass, K. T. Dickerson, K. Stecker, J. Polarek, Biomaterials, vol. 17(11), pp 1101-1108, 1996.
13. "Development of photocrosslinkable Hyaluronic acid-polyethylene glycol-peptide composite hydrogels for soft tissue engineering", J B. Leach, K. A. Bivens, C. N. Collins, C. E. Schmidt, Biomed Mater. Res. 70A, pp 74-82, 2004.

The human skin is the largest organ of the body, accounting for about 16% of the body's weight. It performs many vital roles as both a barrier and a regulating influence between the outside world and the controlled environment within the body.

There are two main layers of skin. The epidermis is made up of keratinocytes, which are stacked on top of each other. The keratinocytes develop at the bottom of the epidermis and rise to the surface, where they are shed as dead, hard, flattened cells. This layer is thus constantly being renewed. Melanocytes and Langerhans cells are other important cells of the epidermis.

The dermis consists mostly of connective tissue and is much thicker than the epidermis. It is responsible for the skin's pliability and mechanical resistance and is also involved in the regulation of body temperature. The dermis supplies the avascular epidermis with nutrients and contains sense organs for touch, pressure, pain and temperature (Meissner's corpuscles, Pacinian corpuscles, free nerve endings), as well as blood vessels, nerve fibers, sebaceous and sweat glands and hair follicles.

The subcutaneous layer is the fatty layer underneath the skin and consists of loose connective tissue and much fat. It acts as a protective cushion, insulates the body by monitoring heat gain and heat loss, and has a strong impact on the way the skin looks.

There are two distinct types of skin aging. Intrinsic aging is genetic in origin, while extrinsic aging is caused by environmental factors, such as exposure to sunlight. Intrinsic aging, also known as the natural aging process, is a continuous process that normally begins in the mid-20s. A number of extrinsic factors often act together with the normal aging process to cause premature aging of the skin. Most premature aging is caused by sun exposure. Other external factors that prematurely age the skin are repetitive facial expressions, gravity, sleeping positions, and smoking.

As the skin ages, the production of cells in the skin slows down and the cells become abnormally shaped, which adversely affects the texture of the skin:
  Younger skin has more fat cells in the dermis than older skin. Thus, older skin looks more transparent and thinner than younger skin.
  Certain components of the skin become depleted with age. The water-retaining and texture-enhancing elements in the intercellular structure such as ceramides, hyaluronic acids, polysaccharides, glycerin, and many others are exhausted and not replenished. Older skin thus tends to be drier than younger skin.
  The skin's support structures, collagen and elastin, deteriorate or become damaged. Wrinkles form in damaged areas of the skin due to the decrease in elastin, collagen, hylauronic acid and other moisturizing reagents.
  Older skin is more subject to allergic reactions, sensitivities, and irritation than younger skin due to a weakened immune system.
  Dead skin cells do not shed as quickly and the turnover of new skin cells may decrease slightly.

For some unknown reason, the skin continues to grow and expand while the supporting fat tissues of the lower layers of skin and the bones decrease. Simultaneously, the facial muscles lose their shape and firmness. The skin thus begins to sag giving the face a drooping appearance.

A huge effort and large investment has been made worldwide aimed at fighting skin aging. Trans-dermal application of collagen, vitamins and moisturizing and firming compounds are available. This requires at least daily application of these substances, due to their very short half-time life in the body.

Another approach is subcutaneous injections of dermal fillers. Permanent fillers are based mainly on silicone derivatives or a collagen matrix with non-biodegradable (poly-methylmethacrylate) spheres. The side effects of dermal filling include fibrosis, teratomas and facial distortions due to dislocation of the filler.

Temporary fillers are based on injections of biodegradable compounds such as collagen, synthetic polymers (cross-linked polyacrylamide, usually classified as hydrogels due to their water swelling and retaining properties); and various modifications of cross linked and stabilized hyaluronic acid. These dermal fillers are injected subcutaneously about every 3-8 months.

Autologus fat implementation has also been used, but this involves a painful and slow healing process.

Hyaluronic acid is known as a biomaterial for use as a controlled release drug delivery matrix[1, 2, 3, 4], scaffolding for tissue engineering cellular procedures[5, 6], and in CA patent 2551121. Use of hyaluronic acid as a biomaterial/tissue engineering matrix utilizes its special properties. It is a soluble, biocompatible polymer, it can be produced from a non-animal source (bacterial fermentation processes) and is produced in a wide range of molecular weights. It is also very easy to chemically modify the HA polymer with various functional groups. It provides a nutritious medium for cell cultures, and its gel form allows control of its flowability. Nevertheless, its most important disadvantage lies in its very short half life time, which, even with an extreme level of cross linking, ranges from few hours to about two weeks[7, 8, 9].

Chemical modification of hyaluronic acid and cross-linking often results in loss of solubility, thus reducing ifs injectability. One of the ways to bypass this barrier is to shape the cross linked HA as a film or layered device[10, 11]/micro particle/bead.

Micro particles of HA disclosed in U.S. Pat. No. 6,969,531, where the particles are processed with chemical reagents (both cross linkers and emulsifying agents, e.g. surfactants).U.S. Pat. No. 7,163,701, discloses HA particles formed in the presence of metal ions.

Linking peptide to a hyaluronic bead or a scaffold is a known approach both as a research tool and as a biomaterial[12, 13]. Nevertheless, this modification also suffers from an increased hydrophobicity, thus reducing the ability of the compound to be injected.

The ficolins form a group of proteins having collagen-, and fibrinogen-like domains. They were first identified as proteins that bind to TGF-β1. Three types of ficolin have been identified in humans: L-ficolin, H ficolin and M ficolin. A ficolin polypeptide consists of a small N-terminal domain, a collagen-like domain, a neck region, and a fibrinogen-like domain, which shows similarity to the C-terminal halves of the beta and gamma chains of fibrinogen. The collagen-like domain mediates the association of ficolin polypeptides into trimers, and the N-terminal domain contains cysteine residues which permit the covalent assembly of trimers into higher oligomers with a "bouquet-like" appearance. This supramolecular organization resembles that of the collectins, a group of C-type lectins which have a C-type CRD in place of the fibrinogen-like domain found in ficolins. Collectins and ficolins are also functionally similar. The collectin mannose binding protein (MBP) is a serum host defense protein in which the C-type CRDs recognize arrays of GlcNAc and mannose residues on pathogen surfaces. MBP initiates the lectin branch of the complement system via activation of MBP-associated proteases (MASPs), leading to elimination of the target pathogen. Two of the three human ficolins, ficolins L and H, are also serum proteins which bind to pathogen surfaces via interaction with carbohydrates (and probably with other molecules), and trigger complement activation though association with MASPs. Ficolin L also acts as an opsonin, promoting phagocytosis of pathogens by neutrophils. Ficolin L polymorphisms affect serum protein levels and sugar binding and may have pathophysiological implications. The third human ficolin, ficolin M, is found in secretory granules in neutrophils and monocytes, recognizes pathogens in a carbohydrate-dependent manner and activates complement via MASPs. Ficolin M may also act as a phagocytic receptor. Ficolins L and H are produced in the liver, in common with MBP, and ficolins M and H are produced in the lung, like the antimicrobial collectins SP-A and SP-D. Human ficolins and MBP also participate in the recognition and clearance of apoptotic cells. Two ficolins, A and B, are present in mouse. Ficolin B is found in the lysosomes of activated macrophages and is suggested to be the ortholog of ficolin M, but it appears that only ficolin A is associated with MASPs and can activate complement. The mouse ortholog of ficolin H is a pseudogene.

SUMMARY OF THE INVENTION

The present invention is based upon the novel and unexpected finding that the protein ficolin is capable of binding to cell surfaces. Most of the research on ficolin refers to its structure (3D) and functionality. It was chosen as the source for our peptides based on its structure and claimed ability to specifically bind N-acetyl gloucoseamine. Based on its 3D structure, peptides were chosen from the tethered arms, potentially available to bind to cells.

Thus, in one of its aspects, the invention provides a pharmaceutical composition for sequestering cells in connective tissue. The composition of the invention comprises a biocompatible scaffolding to which one or more proteins or peptides have been linked, where the peptides or proteins have amino acid sequences that are subsequences of human ficolin and are capable of binding the cells to be sequestered. The cells to be sequestered may be for example, fibroblasts or endothelial cells.

As used herein, the term "connective tissue" refers to any collagen containing tissue of the body, such as dense connective tissue, fibrous connective tissue, elastic connective tissue, adipose tissue, blood.

Without wishing to be bound by a particular theory, it is believed that the pharmaceutical compositions of the invention tend to promote skin rejuvenation by binding and sequestering cells migrating through the skin tissue and immobilizing the cells in the skin tissue. The immobilized cells secrete such substances as collagen, elastin, hyaluronic acid which accumulate in the skin.

The scaffolding of the composition is preferably biodegradable. In a preferred embodiment, the matrix is based on a naturally occurring polymer, existing in the human body, such as a polymer based on hylauronic acid. Hylauronic acid occurs either in dissolved form as in the vitreous humor, synovial fluid and some tumour fluids, or as a gel as in the umbilical cord, in certain mesodermal tumours and in the dermis. Hylauronic acid has been widely used as a dermal filler. It has a high molecular weight, and is considered to be safe. The normal short half life of hylauronic acid in the tissue (due to enzymatic and oxidation-reduction processes) may be slightly extended, for example, by chemical cross-linking which makes the polymer water insoluble that can be formed into particles. This decreases the degradation rate also by decreasing the exposed surface area of the polymer.

In a most preferred embodiment, the scaffolding comprises cross-linked hyaluronic acid or a salt thereof. The hyaluronic acid preferably has a molecular weight in the range of $0.7 \times 10^6$ to $3 \times 10^6$ Dalton. The scaffolding may be in the form of beads, and may be in any form of administration as required in any application.

The composition of the invention may be used as dermal filler. In this case, the composition is preferably in a form suitable for injection. In a preferred embodiment of the invention, the carrier comprises soluble hyaluronic acid. The soluble hyaluronic acid may provide a rapid rejuvenation effect.

The Inventors have found that the following peptides, all having amino acid sequences that are subsequences of the amino acid sequence of human ficolin, may be used in pharmaceutical composition of the invention.

(a) the peptide, referred to herein as "C-Fic" and having the sequence KGYNYSYKSEMKVRPA (SEQ ID NO: 1);

(b) the peptide, referred to herein as "M-Fic" having the sequence GGWTVFQRRVDGSVDFYRK (SEQ ID NO: 2);

(c) the peptide, referred to herein as "C-M-Fic" having the sequence KGYNYSYKVSEMKFQRRVDGSVDFYRK (SEQ ID NO: 3);

(d) the peptide, referred to herein as "C-Fic-a-K" having the sequence KGYKYSYKVSEMKVRPAK (SEQ ID NO: 4);

(e) the peptide, referred to herein as "M-Fic-K" having the sequence GGWTVFQRRMDGSVDFYRK (SEQ ID NO: 5);

(f) the peptide, referred to herein as "C-M-Fic2K" having the sequence KGYKYSYKGGWTVFQRRMDGSVDFYRK (SEQ ID NO: 6);

(g) the peptide, referred to herein as "C-M-Fic-a-K" having the sequence KGYKYSYKVSEMKFQRRMDGSVDFYRK (SEQ ID NO: 7); and (h) the peptide, referred to herein as "C-M-Fic2" having the sequence KGYKYSYKGGWTVFQRRMDGSVDFYR (SEQ ID NO: 8).

In another of its aspects, the invention provides a protein or peptide for use in the pharmaceutical composition of the invention.

The invention further provides use of the pharmaceutical composition of the invention for treating connective tissue, such as dermal connective tissue. For example, the composition may be used as a dermal filler, in which case the composition is preferably in a form suitable for injection. Thus, the invention also provides a dermal filler comprising a biocompatible scaffolding to which one or more proteins or peptides have been linked, where the peptides or proteins have amino acid sequences that are subsequences of human ficolin and are capable of binding predetermined cells.

The invention also provides a method for treating connective tissue comprising introducing into the connective tissue a pharmaceutical composition of the invention. The connective tissue may be, for example, dermal tissue, in which case the composition is preferably administered by injection.

Methods for hyaluronic acid (HA) cross linking are well known in the art. The hyaluronic acid can be cross linked through each of the 3 functional groups attached to its backbone (the carboxylic group, the hydroxylic group, and the acetamido group):

Each repeating unit of hyaluronic acid contains one carboxylate group. These carboxylate group can react with dihydrazides, such as adipic acid dihydrazide, succinic acid dihydrazide, with or without catalysis of EDC and/or sulfo-NHS (complete or partial cross linking).

Each repeating unit of hyaluronic acid contains four hydroxyl groups. These hydroxyl groups can react with di-epoxides, such as 1,4 butanediol diglycidyl ether, poly ethylene glycol diglycidyl ether and poly propylene glycol diglycidyl ether.

The hydroxyl groups can also react with dialdehydes to form acetal/hemiacetal derivatives under acidic conditions—a reaction that will lead to an ether cross linker.

Each repeating group of hyaluronic acid contains one acetamido group, which can go through deacetylization, leaving free amino groups. Amino groups can then cross link via formation of amides, imino or secondary amines.

The carboxylic group of the hyaluronic acid can react with a water soluble carbodimide to form O-acylisourea, which then will react with neighboring carboxyl to form an anhydride, which then will react with an hydroxyl group to give both inter- and intra-molecular crosslinks.

In one preferred embodiment of the invention, the cross linking reaction is the basis for bead formation. Soluble gels can be emulsified in corn oil, MCT (Medium Chain Triglycerides) oil or another suitable oil, heated to 60° C., and then cross linked to form a drop shape. The particle size of the bead can be determined by the mixing speed of the reversed emulsion. The reaction is performed under elevated temperature to accelerate the process and also for drying the beads.

The cross-linked beads may be precipitated by addition of an organic solvent such as ethanol, IPA (iso Propyl Alcohol), acetone, hexane or the like. Being water insoluble, the beads can be purified by washing with water.

The level of crosslinking may be selected to endow the beads with a desired rigidity and stability, while leaving active groups, mainly carboxyl groups available for peptide binding.

The peptides of the composition can be activated for linkage to the scaffolding, for example, by succinic anhydride to give peptide-hemisuccinate, which can then be reacted in the presence of EDC/sulfo-NHS either with free carboxylates or with free tails of epoxide, or hydrazone depending on the cross linker used. The peptides can be activated and attached to the HA prior to cross linking.

Thus, in one of its aspects, the present invention provides a pharmaceutical composition for sequestering cells in connective tissue comprising:

(a) a biocompatible scaffolding;
(b) one or more peptides or proteins selected from:
  (i) a peptide or protein having an amino acid sequence that is a subsequence of human ficolin capable of binding the cells to be sequestered; and
  (ii) a peptide or protein having a sequence homology of at least 70% with a peptide of (i) and capable of binding the cells to be sequestered; the peptide being linked to the scaffolding; and
(c) a physiologically acceptable carrier.

In another of its aspects, the invention provides a protein or peptide for use in the pharmaceutical composition according to any one of the previous claims.

The invention also provides use of the pharmaceutical composition according to any one of the previous claims for treating connective tissue.

The invention further provides use of a protein or a peptide for the preparation of the pharmaceutical composition of the invention.

The invention in yet another of its aspects provides a dermal filler comprising:
(a) a biocompatible scaffolding;
(b) one or more peptides or proteins selected from:
  (i) a peptide or protein having an amino acid sequence that is a subsequence of human ficolin capable of binding one or more predetermined cell types; and
  (ii) a peptide or protein having a sequence homology of at least 70% with a peptide of (i) and capable of binding the predetermined cell types.

The invention also provides a method for treating connective tissue comprising introducing into the connective tissue a pharmaceutical composition of the invention.

BRIEF DESCRIPTION OF THE DRAWINGS

In order to understand the invention and to see how it may be carried out in practice, embodiments will now be described, by way of non-limiting example only, with reference to the accompanying drawings, in which.

EXAMPLES

Materials and Methods

Figure 1:
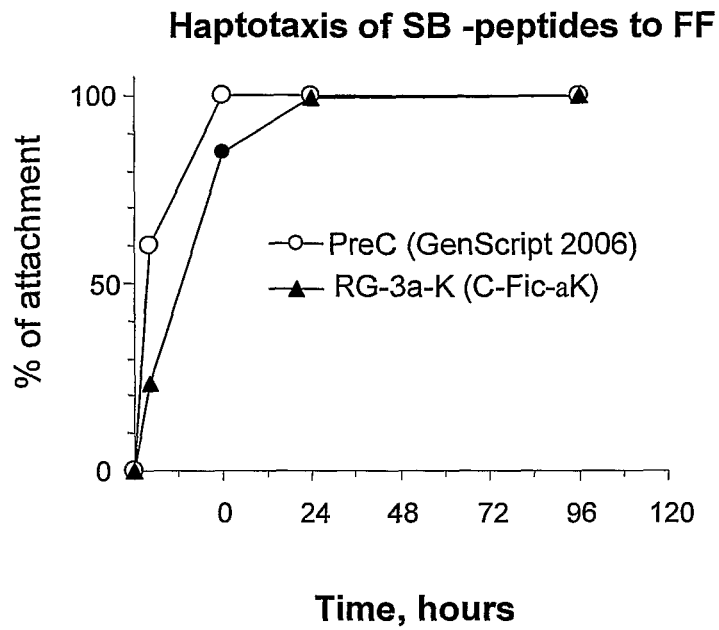
FIG. 1 shows cell binding of FF1 to PreC and C-Fic-aK, 6 mg peptide/ml.

Solutions:
a. 1 mM HCl solution for activation of CNBr Sepharose beads at 4° C.
b. Coupling buffer containing 0.1 M NaHCO$_3$ and 0.5 N NaCl adjusted to pH 8.3.
c. Blocking solution to block remaining active groups on the SEPHAROSE BEADS gel containing 0.2M Glycine, pH 8.0 at 4° C.
d. Acetate buffer containing 0.1 M Acetate buffer pH 4.0, 0.5 M NaCl Peptide solutions: Table 1 shows the peptides that were used.

TABLE 1

| Peptide | Sequence | ID |
|---|---|---|
| C-Fic | KGYNYSYKSEMKVRPAK | SEQ ID NO: 1 |
| M-Fic | GGWTVFQRRVDGSVDFYRK | SEQ ID NO: 2 |
| C-M-Fic | KGYNYSYKVSEMKFQRRVDGSVDFYRK | SEQ ID NO: 3 |
| C-Fic-a-K | KGYKYSYKVSEMKVRPAK | SEQ ID NO: 4 |
| M-Fic-K | GGWTVFQRRMDGSVDFYRK | SEQ ID NO: 5 |
| CM-Fic-a-K | KGYKYSYKVSEMKFQRRMDGS-VDYRK | SEQ ID NO: 6 |
| CM-Fic-2 | KGYKYSYKGGWTVFQRRMDGSVDFYR | SEQ ID NO: 7 |
| CM-Fic-2K | KGYKYSYKGGWTVFQRRMDGSVDFYRK | SEQ ID NO: 8 |
| Controls | | |
| C-M-g | KTRWYSMKKTTMKVFQKRLVGSVDFKK | SEQ ID NO: 9 |
| preCγ | KTRWYSMKKTTMKIIPFNR | SEQ ID NO: 10 |

Peptide solutions (2 mg/ml) were prepared in coupling buffer. For insoluble peptides the dry peptides were pre-dissolved in 50 µl DMSO before the addition of the coupling buffer. The exact concentration of the peptide solutions was determined spectrophotometrically at OD$_{280}$.

Coupling Peptides to Sepharose Beads 100 mg of dried CNBr-Sepharose Beads (yields 350 µl of swollen Sepharose Beads—gel) was introduced into a disposable polystyrene mini-column (FIG. 1), appropriate for the preparation of a 0.5-2 ml gel filtration column (Pierce, Prod #29920). The lower part of the columns is blocked by a thick glass filter and a stopper.

3-4 ml total volume of HCl solution (1 mM) was added to the column, and the liquid was forced to flow under vacuum pressure through the gel. This process was repeated 5 times. The final aliquot of HCl was aspirated until cracks appeared in the gel cake. 2-3 ml aliquots of coupling buffer were immediately added to the washed beads and aspirated. This step was repeated 4-5 times. The high pH hydrolyzes and opens the active groups.

Peptide Binding

A peptide solution in coupling buffer prepared as above was immediately added to the activated SEPHAROSE BEADS Sepharose beads were used to fixate the peptides for all in-vitro assays in the column to a final binding of 6 mg peptide per ml SEPHAROSE BEADS gel. The column was closed and shaken overnight at 4° C. very gently to avoid mechanical breakage of SEPHAROSE BEADS. The bottom cap of the column was removed and the solution of ligand/buffer was collected as the Sepharose Beads settled on the filter. The $OD_{280}$ of the collected buffer was checked to determine the concentration of uncoupled peptide. The gel was washed/aspirated with 5 volumes (~2 ml) of coupling buffer and gently mixed. Any remaining active groups on the gel were blocked with blocking buffer for 2 hours at room temperature or overnight at 4° C. The Sepharose Beads gel with peptides was then washed by 2 cycles each of 5 gel volumes of:
 a. 0.1 M Acetate buffer
 b. Coupling buffer
 c. Storing buffer: azide-coupling buffer: coupling buffer containing 0.1% $NaN_3$ (final concentration)

The Sepharose Beads were stored for till use at 4-8° C. Prior to use, the beads were in an Eppendorff tube 4 times for 3 min each with PBS or medium.

Cell Attachment Assay in Monolayers

The tested peptides (Table 1) were coupled to Sepharose Beads at two concentrations: 6 and 12 mg/ml Sepharose Beads. Sepharose Beads that underwent the coupling procedure without peptide addition ("naked Sepharose Beads") served as a negative control (referred to herein as "Sepharose Beads—blank"). A cell binding assay was performed with 2 normal cell types: bovine aortal endothelial cells (BAEC) and human foreskin fibrobalsts (FF1). Sepharose Beads were added to 12 well culture plates with sub-confluent monolayer of the cultured cells (100-300 beads were added to each well). The fraction of Sepharose Beads attached to the monolayer was monitored at different times.

Cell Attachment Assay in Cell Suspensions.

Attachment of FF1 in suspension to peptides bound to sepharose beads was followed using the MTS assay. The MTS assay uses tetrazolium, which is taken up by viable cells and converted into formazan, which has a light absorption peak at 492 nm. The light absorbance at 492 ($OD_{492}$) is directly proportional to the number of the living cells attached to the beads. Calibration curves were used to transform the $OD_{492}$ readings into cell number, Results FIG. 1 shows cell binding of FF1 to PreC and C-Fic-aK, 6 mg peptide/ml. The results indicate a similar rate of cell binding of the tested peptide compared with the positive control. Both peptides reach 100% cell binding within less than 24 hours.

Figure 2:
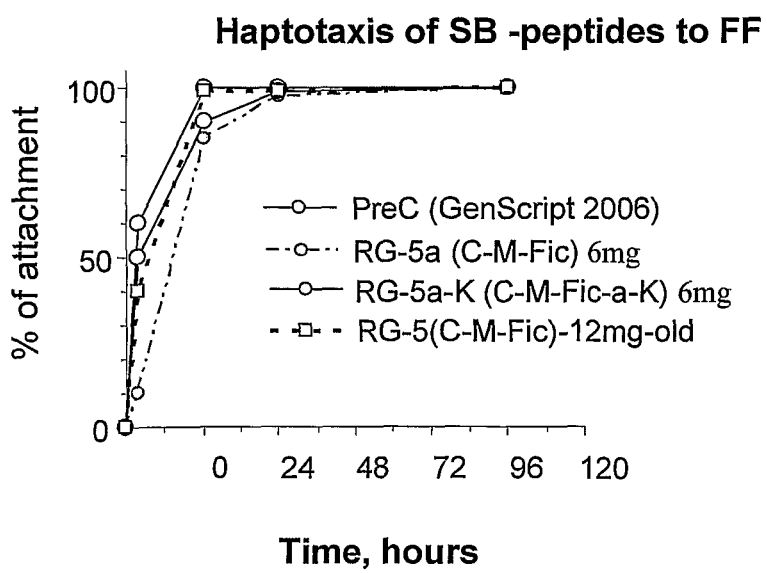
FIG. 2 shows cell binding of FF1 to PreC, C-M-Fic, and C-M-Fic-a-K at a concentration of 6 mg peptide/ml, and the peptide C-M-Fic at a concentration of 12 mg peptide'.

FIG. 2 shows cell binding of FF1 to PreC, C-M-Fic, and, C-M-Fic-a-K at a concentration of 6 mg peptide/ml, and the peptide C-M-Fic at a concentration of 12 mg peptide. All of the peptides tested bound the cells with a similar kinetics as the positive control protein PreC. The higher concentration of the peptide C-M-Fic (12 mg/ml) showed a slightly faster cell binding compared to the lower concentration (6 mg/ml). Modifying the peptide C-M-Fic to produce the peptide C-M-Fic-aK accelerated the kinetics of cell binding.

Figure 3A:
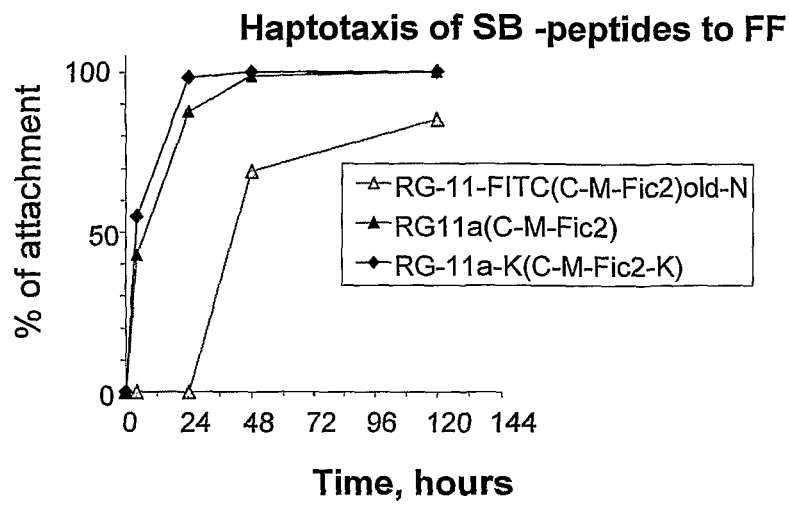
FIG. 3a shows cell binding of FF1 to C-M-Fic2.

FIG. 3a shows cell binding of FF1 to C-M-Fic2. C-M-Fic2-K differs from C-M-Fic2 by the addition of a lysine group. Both C-M-Fic2 and C-M-Fic2-K show a good kinetic profile of cell binding (fast attachment), and reach 100% binding. Nevertheless, an addition of a FITC group (highly hydrophobic) inhibits both the rate and probably the total extent of cell binding.

Figure 3B:
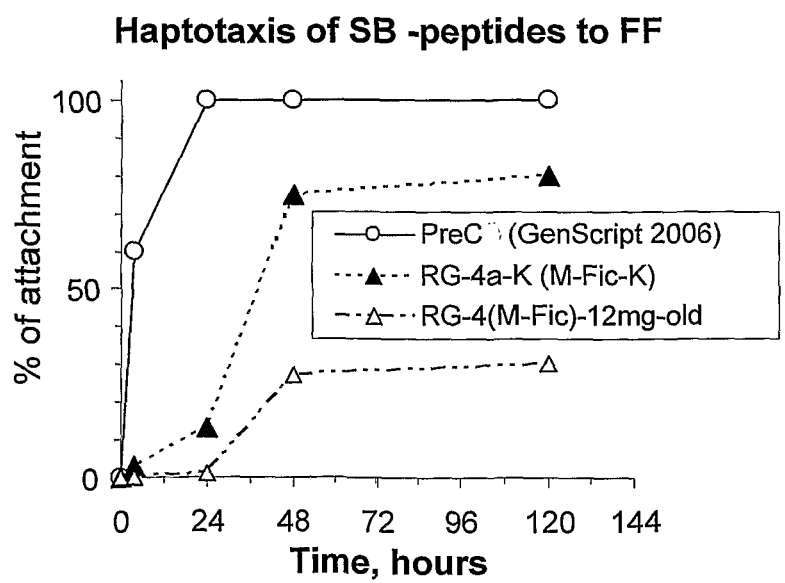
FIG. 3b shows the activity of M-fic-K, and M-Fic in comparison with the positive control PreC-gamma, 6 mg peptide/ml.

FIG. 3b shows the activity of M-fic-K, and M-Fic in comparison with the positive control PreC-gamma, 6 mg peptide/ml. As observed also in the comparison of C-M-Fic2 and C-M-Fic2-K (FIG. 3a), the addition of a lysine group resulted a dramatic change in activity, although M-Fic was initially inferior to the positive control.

Figure 4A:
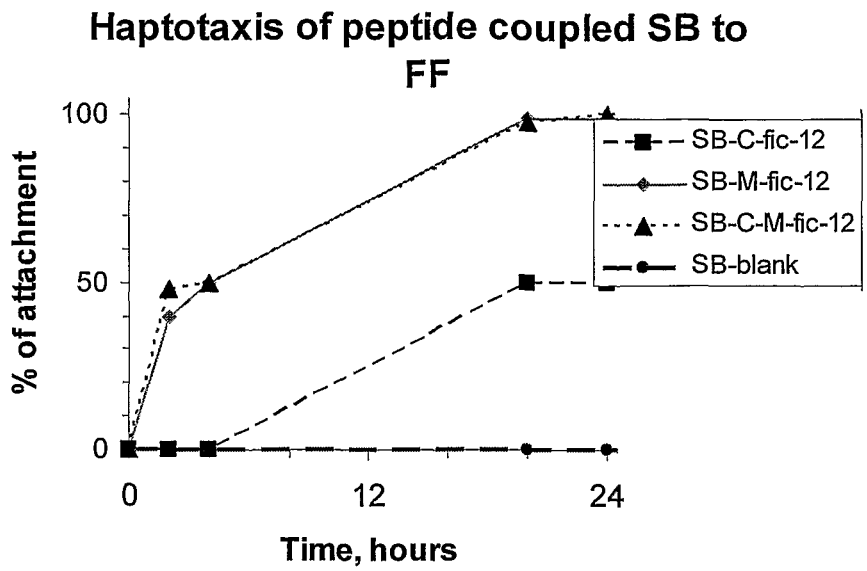
FIG. 4 shows cell binding of FF1 to C-M-Fic, M-Fic, and C-Fic over a period of 24 hours (FIG. 4a) and 150 hours (FIG. 4b)
Figure 4B:
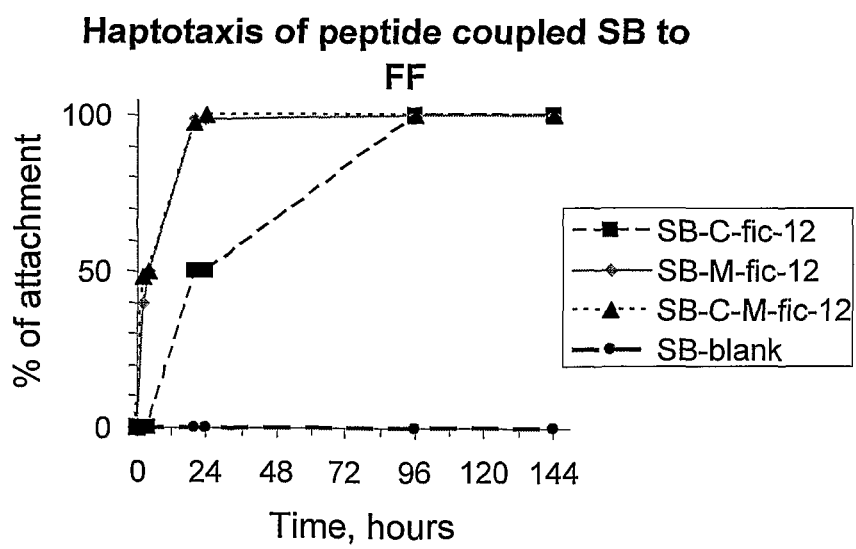
Figure 5A:
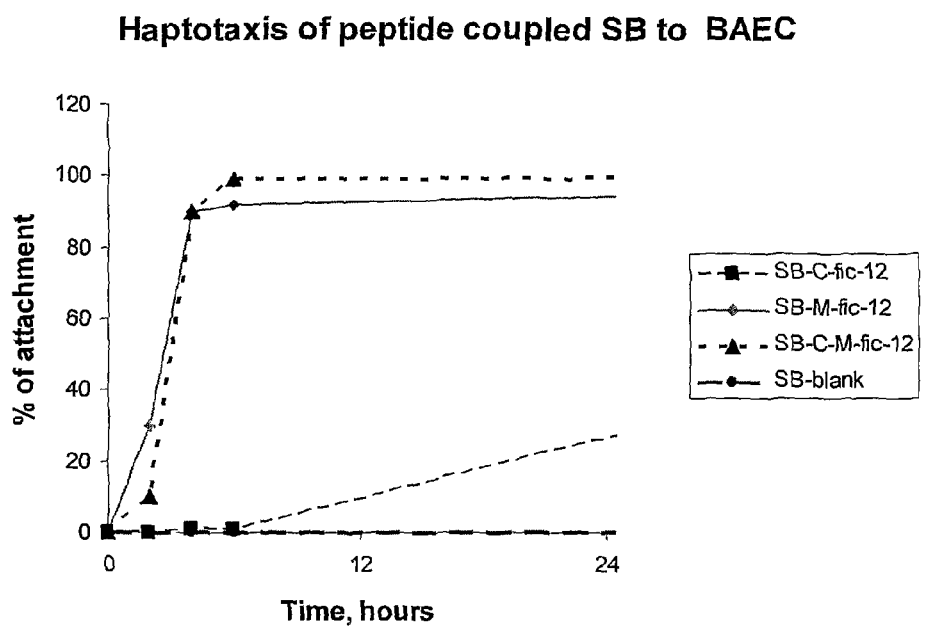
FIG. 5 shows cell binding of BAEC to C-M-Fic, M-Fic, and C-Fic over a period of 24 hours (FIG. 5a) and 150 hours (FIG. 5b)
Figure 5B:
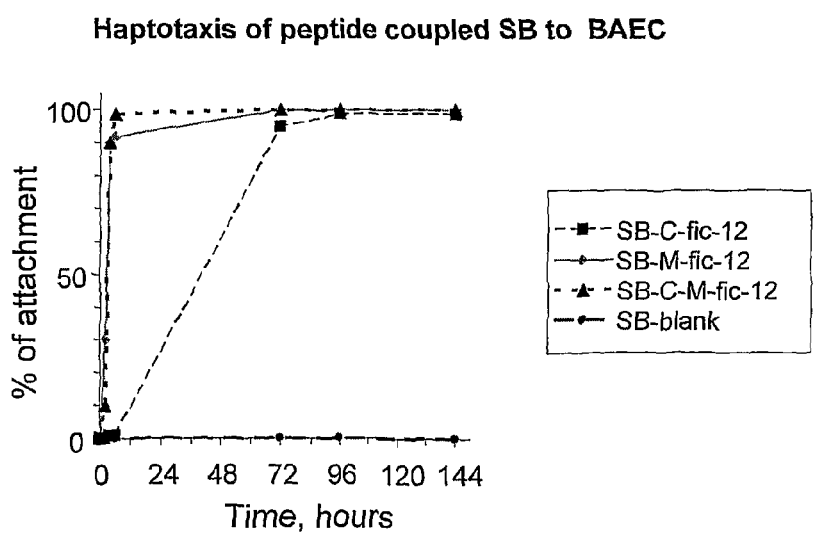

FIG. 4 shows cell binding of FF1 to C-M-Fic, M-Fic, C-Fic and blank (uncoated beads), at 12 mg peptide/ml concentration, over 24 hours (FIG. 4a). Blank sepharose beads do not have any cell binding capability, therefore confirming the peptides as the source of binding. Various kinetic profiles of different peptides can be shown, already within the first 12 hours. Some show a lag time before cell binding, whereas others show an immediate response. The peptides also differ in their maximal capacity for binding (some reach 100% and some bind about 50% of the cells). FIG. 4b shows the same list of peptides after 150 hours. Of particular interest is the observation that even the slower peptide (C-Fic) reaches 100% cell binding after a period of time, FIG. 5 shows cell binding of BAEC to C-M-Fic, M-Fic, C-Fic and blank, 12 mg peptide/ml concentration, over 24 hours (FIG. 5a). As in the previous test group of peptides—various profiles are detected. FIG. 5b follows the BAEC binding after 150 hours, where all peptides reach complete cell binding.

Figure 6A:
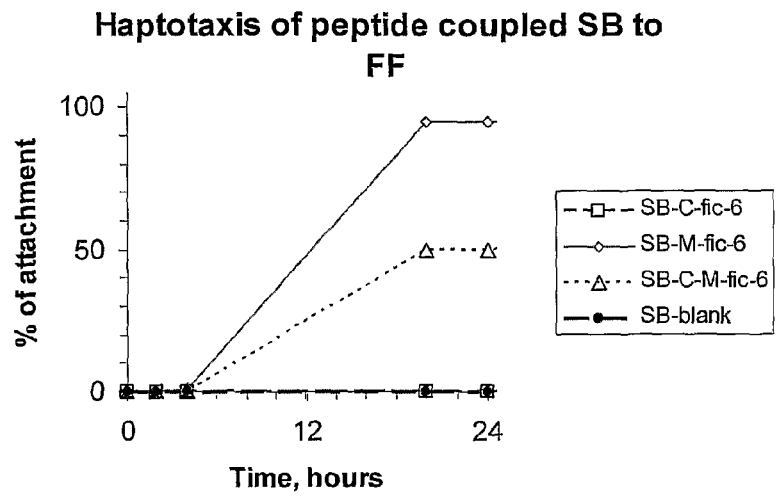
FIG. 6 shows cell binding of FF1 to C-M-Fic, M-Fic, and C-Fic at 6 mg peptide/ml over a period of 24 hours (FIG. 6a) and 150 hours (FIG. 6b)
Figure 6B:
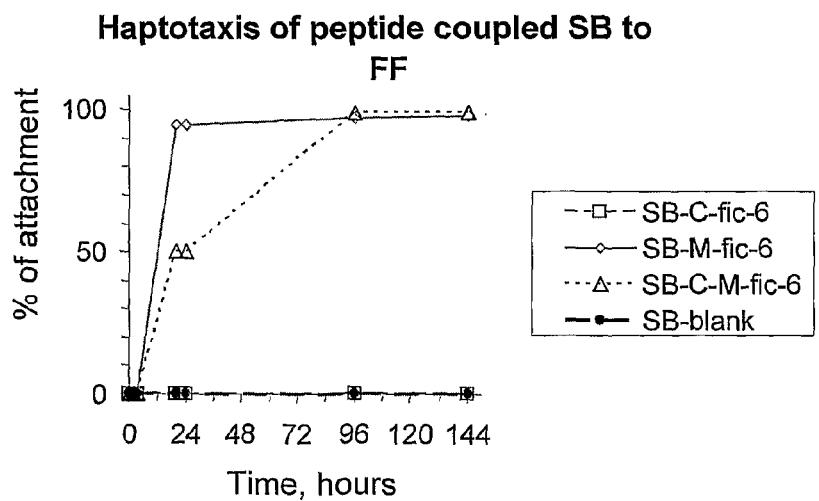

FIG. 6 shows cell binding of FF1 to C-M-Fic, M-Fic, C-Fic and blank (6a after 24 hours, and 6b after 150 hours), at 6 mg peptide/ml concentration, over 24 hours (FIG. 6a). Comparing the results to FIG. 4, an evident decrease in binding rate is observed. This is a dose response test, allowing differentiation between the active peptides at 12 mg/ml. C-fic looses its activity, C-M-fic is strongly affected by the lowerdose, whereas M-fic seems to retain most of its activity.

Figure 7A:
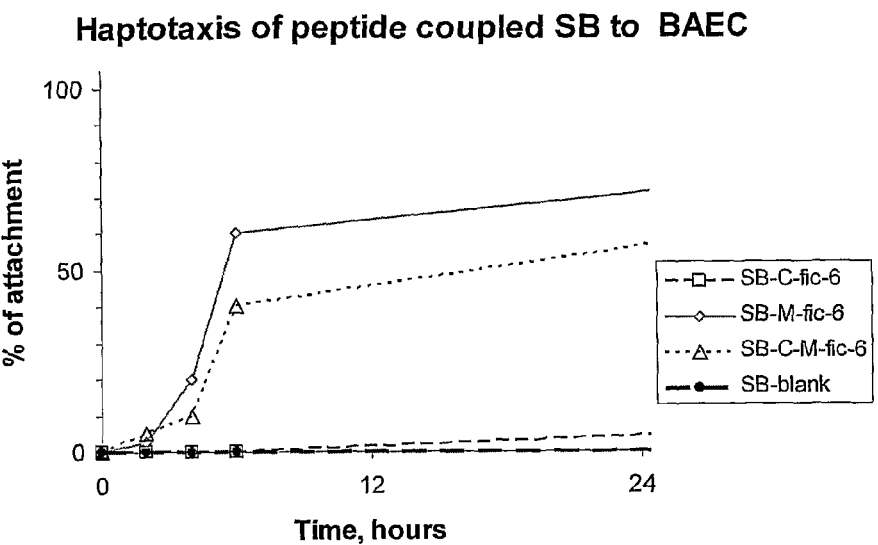
FIG. 7 shows cell binding of BAEC to C-M-Fic, and M-Fic, C-Fic at 6 mg peptide/ml a period of 24 hours (FIG. 7a) and 150 hours (FIG. 7b)
Figure 7B:
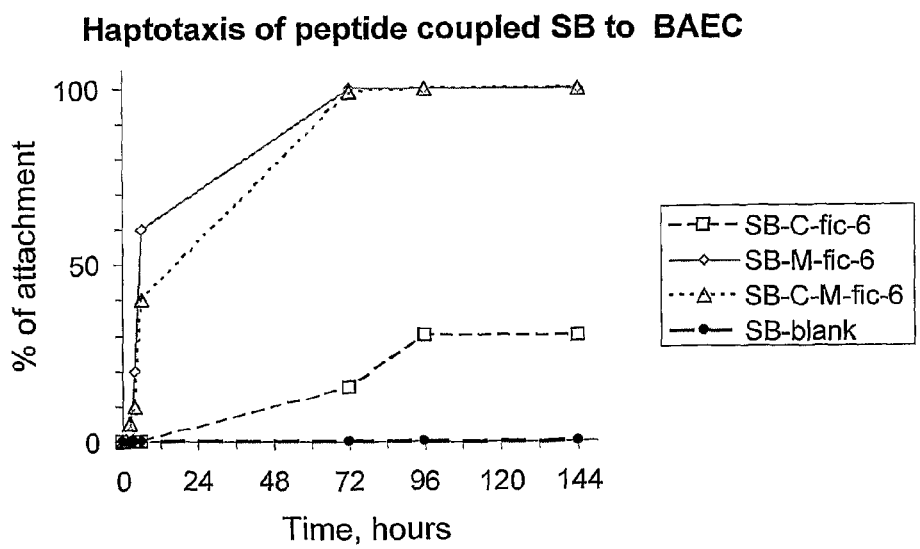

FIG. 7 shows cell binding of BAEC to C-M-Fic, M-Fic, C-Fic and blank, 6 mg peptide/ml, over 24 hours (FIG. 7a) and 150 hours (FIG. 7b). Compared with the 12 mg/ml results (FIG. 5) the BAEC seem to be more sensitive to the dose decrease. This is evident both in the short term and in the longer term.

Figure 8A:
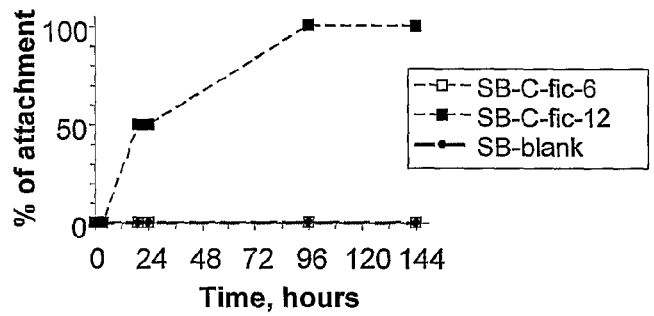
FIG. 8 shows the dose responses of cell binding of FF1 to sepharose beads coated with the peptides C-Fic-6 and C-Fic-12 (FIG. 8a), the peptides M-Fic-6 and M-Fic-12 (FIG. 8b); and the peptides C-M-Fic-6 and C-M-Fic-12 (FIG. 8c)
Figure 8B:
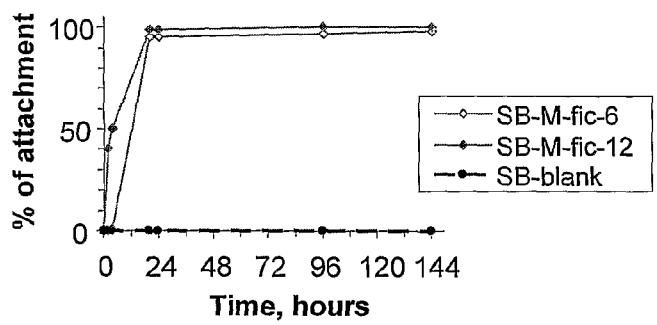
Figure 8C:
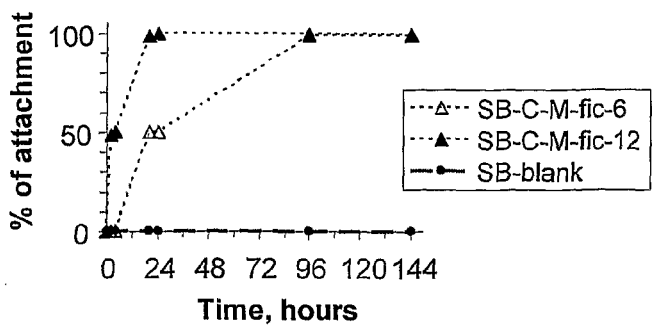

FIG. 8 shows the dose responses of cell binding of FF1 to sepharose beads coated with one of the peptides, or with no coat (SB-blank). C-Fic (FIG. 8a), has no reactivity at 6 mg/ml. M-Fic (FIG. 8b,) retains its activity at the lower concentration. Cell binding of FF1 to C-M-Fic (FIG. 8c) is strongly affected by the decrease and reaches 100% cell binding only after 96 hrs (compared to 20 hrs in the higher dose). The results presented in FIG. 8 are over 150 hours.

Figure 9A:
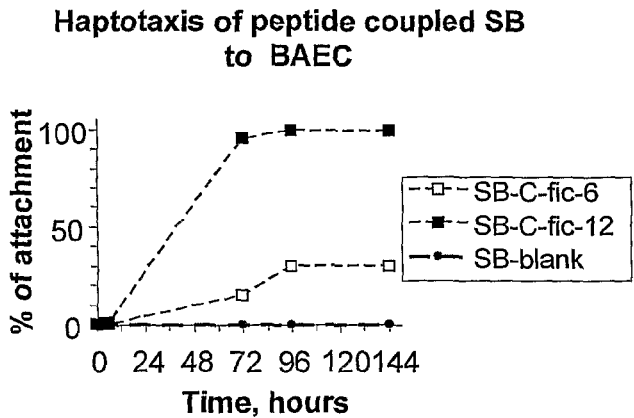
FIG. 9 shows the dose responses of cell binding of BAEC to the peptides C-Fic-6 and C-Fic-12 (FIG. 9a), the peptides M-Fic-6 and M-Fic-12 (FIG. 9b); and the peptides C-M-Fic-6 and C-M-Fic-12 (FIG. 9c)the various peptides.
Figure 9B:
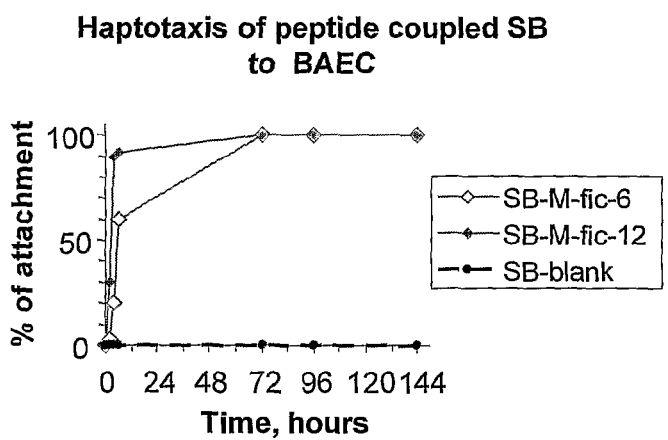
Figure 9C:
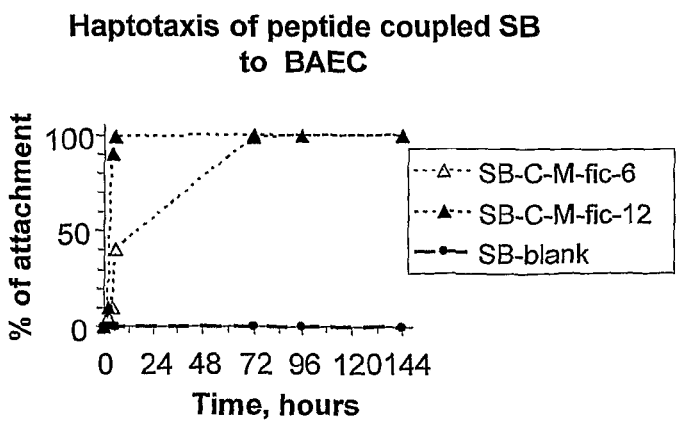

FIG. 9 shows the dose responses of cell binding of BAEC to each peptide. C-Fic (FIG. 9a), completely looses reactivity at 6 mg/ml. There is a slight decrease in M-Fic binding rate at the lower concentration (FIG. 9b), and cell binding of BAEC to C-M-Fic (FIG. 9c) has a slower rate at the lower concentration.

The following conclusions could be drawn:
1. Sepharose Beads alone did not attach to the cell monolayer of either cell type. Therefore the reactivity of cell binding shown in all the other experiments can be attributed to the peptides.
2. At a concentration of 12 mg peptide/ml, all of the tested peptides reach a 100% cell binding at a relatively short time, both with FF1 and BAEC.
3. In general BAEC interacted with the peptides faster than FF1.
4. A dose response approach was tested, in order to fine tune the screening between the various peptides.
5. Even at a concentration of 6 mg/ml, M-fic reached saturated cell binding within 24 hrs. C-M-fic reached saturated cell binding within 96 hrs. At this concentration, C-fic was inactive. For BAEC, similar results were obtained, but for these cells C-fic also showed some activity.

Figure 10:
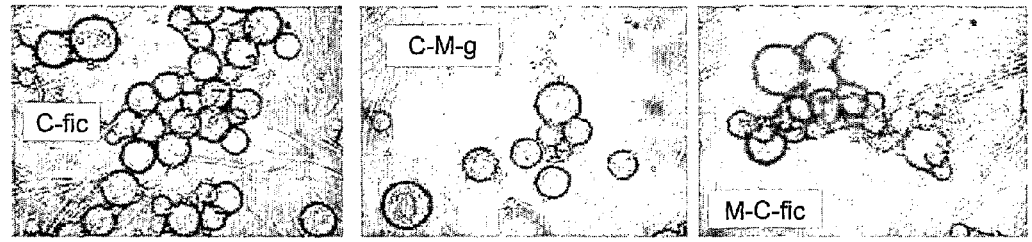
FIG. 10 shows Nomarsky optics microscopy of peptide coated beads following attachment to FF1 after 3 days of incubation, (×100) (left panel, C-Fic, middle panel C-M Fic, right panel M-C-Fic)

FIG. 10 shows Nomarsky optics microscopy of peptide coated beads following attachment to FF1 after 3 days of incubation, (×100) (left panel, C-Fic, middle panel C-M Fic, right panel M-C-Fic). Note the aggregates of cells and beads formed with the peptides M-fic, C-M-Fic.

Figure 11:
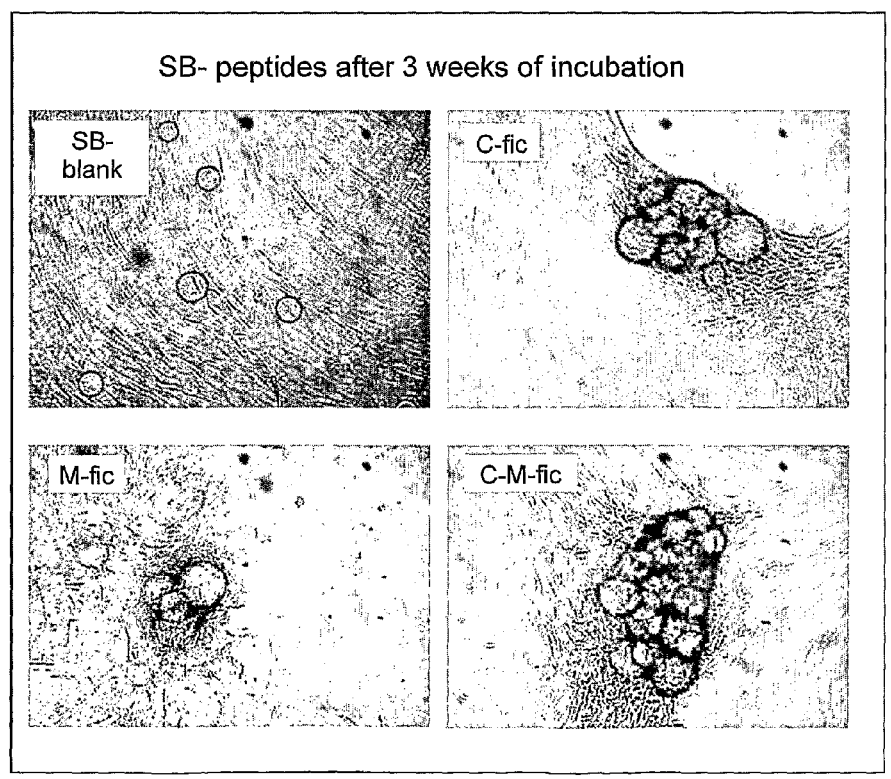
FIG. 11 shows Nomarsky optics microscopy of peptide coated beads and their attachment to FF1 after 3 weeks of incubation, (×100) (Upper left panel, blank, upper right panel C-Fic, lower left panel M-fic, lower right panel, C-M-Fic)

FIG. 11 shows Nomarsky optics microscopy of peptide coated beads and their attachment to FF1 after 3 weeks of incubation, (×100). (Upper left panel, blank, upper right panel C-Fic, lower left panel M-fic, lower right panel, C-M-Fic). The same response is seen as in FIG. 10, but in places where the cells aggregated, the aggregate was more pronounced even with less active peptides.

Figure 12:
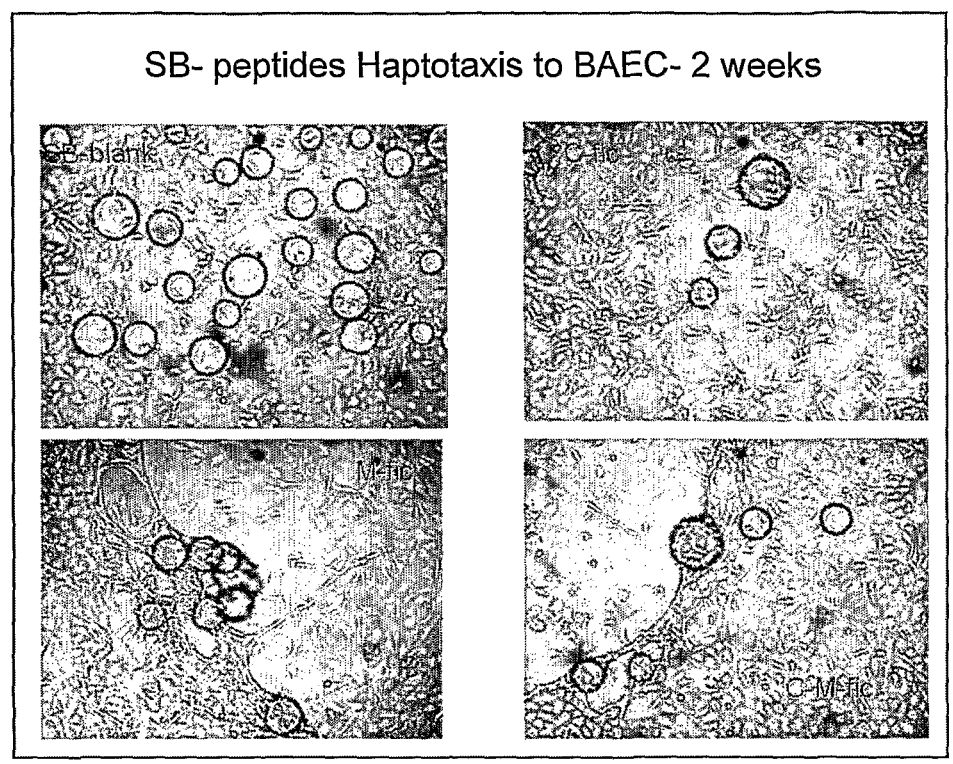
FIG. 12 shows Nomarsky optics microscopy of peptide coated beads and their attachment to endothelial cells (BAEC) following 3 weeks of incubation, (×100) (Upper left panel, blank, upper right panel C-Fic, lower left panel M-fic, lower right panel C-M-Fic)

FIG. 12 shows Nomarsky optics microscopy of peptide coated beads and their attachment to endothelial cells (BAEC) following 3 weeks of incubation, (×100). (Upper left panel, blank, upper right panel C-Fic, lower left panel M-fic, lower right panel C-M-Fic). Note the formation of small tubes associated with sepharose beads bound to M fic and CM-fic.

At longer incubation times, the peptides further immobilized FF1 to the beads forming stable bead-cell aggregates. This attachment increased with time without loss of the effect, as shown in FIGS. 10 and 11 for the different peptides tested. sepharose beads coated with the active peptides form on the plate 3-D structures at a high cell density.

With BAEC, the cells were mobilized to the same peptides. In FIG. 12 it is evident that the sepharose beads coated with the active peptides induced aggregate and tube like structures.

M-fic was of the highest activity and C-M-Fic was also active.

Toxicity Assay for the Different Peptides:

A toxicity assay was done to determine the toxicity of the peptides tested to either one of the cell lines used. $15 \times 10^3$ cells (FF1 or BAEC) were seeded in 96 well plastic plates. After an overnight incubation, increasing concentrations of peptides in the range of 0.1-300 µg/ml were added to the wells. Cell survival was checked by the MTS assay after 2 and 5 days and normalized to the cell number of the controls (no peptide).

Figure 13A:
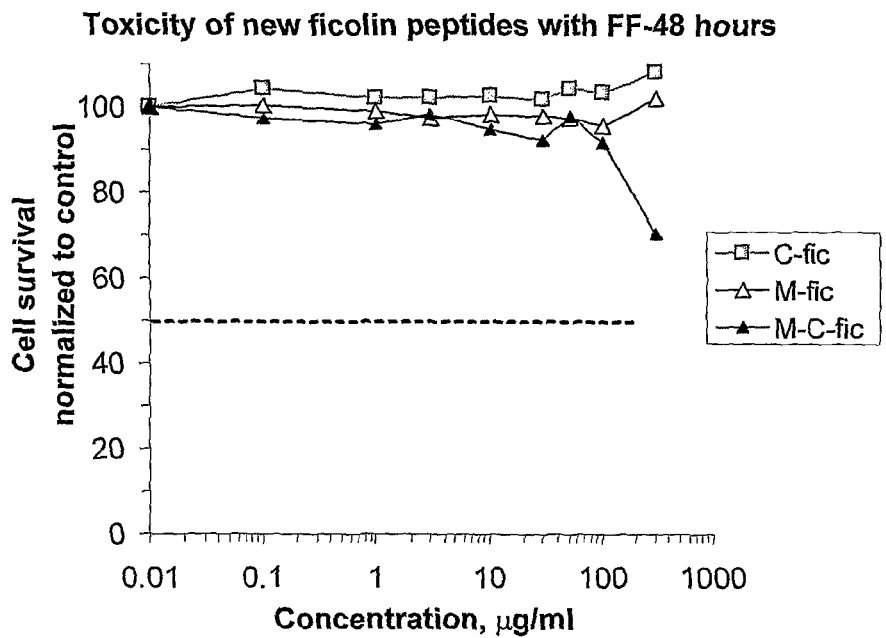
FIG. 13 shows the toxicity of C-Fic, M-Fic, and M-C-Fic to FF1 cells (FIG. 13a) and BAEC (FIG. 13b) over a wide range of peptide concentration after 48 hours.
Figure 13B:
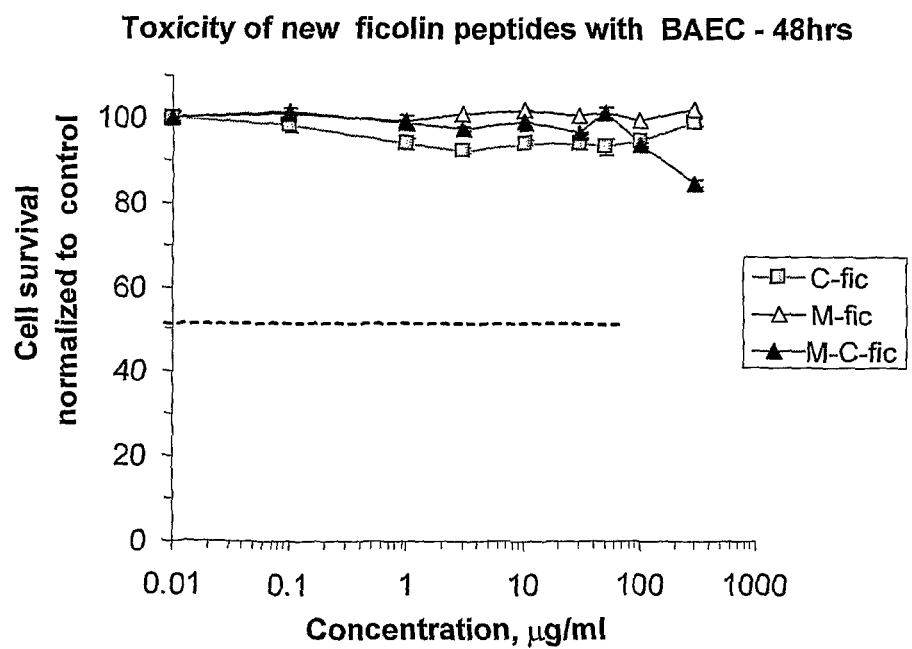
Figure 14A:
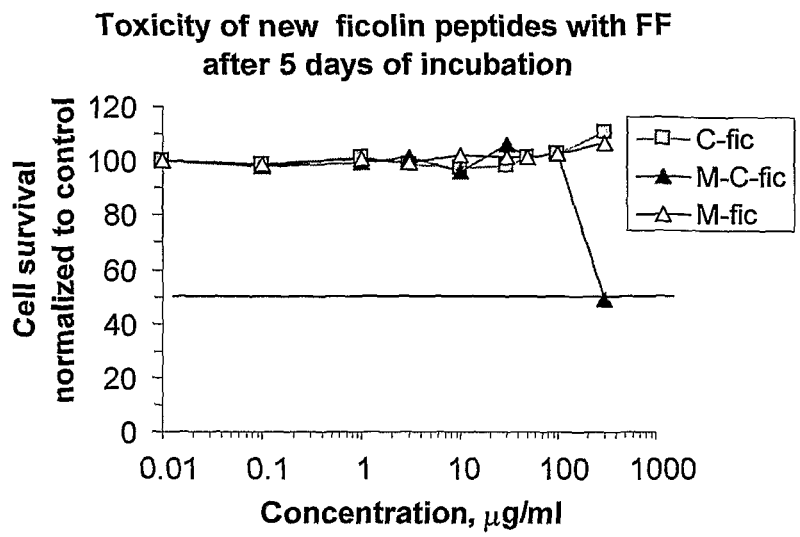
FIG. 14 shows the toxicity of the various peptides to FF1 cells (FIG. 14a) and BAEC (FIG. 14b) after 5 days of incubation.
Figure 14B:
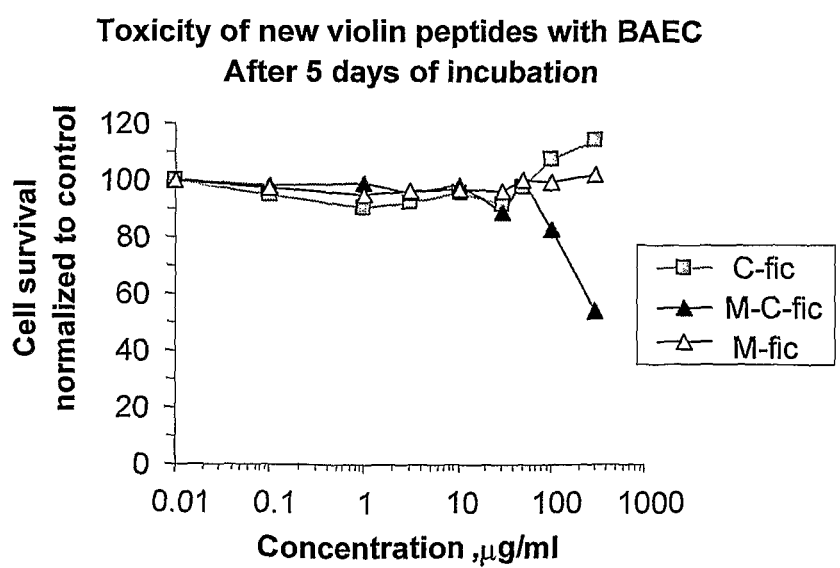

FIG. 13 shows the toxicity of C-Fic, M-Fic, and M-C-Fic to FF1 cells (FIG. 13a) and BAEC (FIG. 13b) over a wide range of peptide concentration after 48 hours. FIG. 14 shows the toxicity of the various peptides to FF1 cells (FIG. 14a) and BAEC (FIG. 14b) after 5 days of incubation.

Attachment of Cells in Suspension to Peptide—Bead Constructs.

Figure 15:
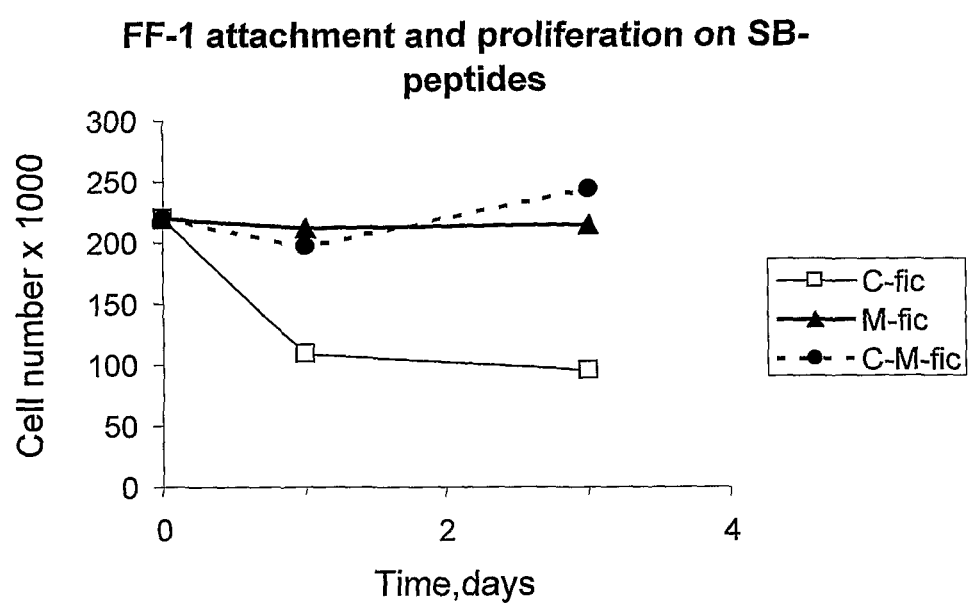
FIG. 15 shows the attachment of FF1 cells in suspension to the coated sepharose beads.

FIG. 15 shows the attachment of FF1 cells in suspension to the coated sepharose beads. For C-fic and CM-fic coated beads, cell attachment was stable for at least three days. For C-M-fic, an increase in cell number is detected after the first day, indicating a proliferation of cells. For C-fic coated beads, cell attachment decreased during the first day and then remained stable.

Conclusions
1. In general, the peptides at the lower peptide concentration of 6 ml/mg attached at a slower rate to either cell type in comparison to the higher concentration (12 mg/ml).
2. C-fic at a concentration of 6 mg peptide/ml did not attach to FF1 or to BAEC. The extent of cell binding was about 30% after 96 hours of incubation.
3. M-fic and C-M-fic reached saturated attachment after 72 hours of incubation.
4. Most of the peptides were not toxic in a wide range of concentrations tested. At very high concentrations (>100 µg/ml), some enhancement of proliferation was observed for some of the peptides.
5. C-M-fic showed some minor toxicity at very high concentrations (>100 µg/ml) for both cell types and prolonged exposure (5 days). At high concentrations of this peptide, cell survival, normalized to controls, was about 50%.

The invention claimed is:

1. A pharmaceutical composition for sequestering cells in connective tissue, comprising:
   a. a biocompatible scaffolding linked to one or more peptides at least 70 percent homologous to one or more peptides comprising the sequences of KGYNYSYKSEMKVRPA (SEQ ID NO: 1), GGWTVFQRRVDGSVDFYRK (SEQ ID NO: 2), KGYNYSYKVSEMKFQRRVDGSVDFYRK (SEQ ID NO: 3), KGYKYSYKVSEMKVRPAK (SEQ ID NO: 4), GGWTVFQRRMDGSVDFYRK (SEQ ID NO: 5), KGYKYSYKGGWTVFQRRMDGSVDFYRK (SEQ ID NO: 6), KGYKYSYKVSEMKFQRRMDGSVDFYRK (SEQ ID NO: 7), or KGYKYSYKGGWTVFQRRMDGSVDFYR (SEQ ID NO: 8); and
   b. a physiologically acceptable carrier.

2. The pharmaceutical composition according to claim 1, wherein the cells to be sequestered are selected from fibroblasts and endothelial cells.

3. The pharmaceutical composition according to claim 1, wherein the biocompatible scaffolding is linked to one or more peptides comprising the sequences of KGYNYSYKSEMKVRPA (SEQ ID NO: 1), GGWTVFQRRVDGSVDFYRK (SEQ ID NO: 2), KGYNYSYKVSEMKFQRRVDGSVDFYRK (SEQ ID NO: 3), KGYKYSYKVSEMKVRPAK (SEQ ID NO: 4), GGWTVFQRRMDGSVDFYRK (SEQ ID NO: 5), KGYKYSYKGGWTVFQRRMDGSVDFYRK (SEQ ID NO: 6), KGYKYSYKVSEMKFQRRMDGSVDFYRK (SEQ ID NO: 7), or KGYKYSYKGGWTVFQRRMDGSVDFYR (SEQ ID NO: 8).

4. The composition according to claim 1, wherein the biocompatible scaffolding is biodegradable.

5. The composition according to claim 1, wherein the biocompatible scaffolding is in the form of beads.

6. The composition according to claim 1, wherein the biocompatible scaffolding comprises hyaluronic acid or a salt thereof.

7. The composition according to claim 6, wherein the hyaluronic acid or the salt thereof is cross-linked.

8. The composition according to claim 6, wherein the hyaluronic acid or the salt thereof has an average molecular weight in the range of $0.7 \times 10^6$ to $3 \times 10^6$ Dalton.

9. The composition according to claim 7, wherein the hyaluronic acid or the salt thereof is cross-linked is via any one or more of carboxylic groups, hydroxyl groups or acetamido groups.

10. The pharmaceutical composition according to claim 1, in a form suitable for injection.

11. An isolated peptide comprising the sequence selected from the group consisting of KGYNYSYKSEMKVRPA (SEQ ID NO: 1), GGWTVFQRRVDGSVDFYRK (SEQ ID NO: 2), KGYNYSYKVSEMKFQRRVDGSVDFYRK (SEQ ID NO: 3), GGWTVFQRRMDGSVDFYRK (SEQ ID NO: 5), KGYKYSYKGGWTVFQRRMDGSVDFYRK (SEQ ID NO: 6), KGYKYSYKVSEMKFQRRMDGSVDFYRK (SEQ ID NO: 7), and KGYKYSYKGGWTVFQRRMDGSVDFYR (SEQ ID NO: 8).

12. A dermal filler, comprising: (a) a biocompatible scaffolding; and (b) one or more peptides at least 70 percent homologous to one or more peptides comprising the sequences of KGYNYSYKSEMKVRPA (SEQ ID NO: 1), GGWTVFQRRVDGSVDFYRK (SEQ ID NO: 2), KGYNYSYKVSEMKFQRRVDGSVDFYRK (SEQ ID NO: 3), KGYKYSYKVSEMKVRPAK (SEQ ID NO: 4), GGWTVFQRRMDGSVDFYRK (SEQ ID NO: 5), KGYKYSYKGGWTVFQRRMDGSVDFYRK (SEQ ID NO: 6), KGYKYSYKVSEMKFQRRMDGSVDFYRK (SEQ ID NO: 7), and KGYKYSYKGGWTVFQRRMDGSVDFYR (SEQ ID NO: 8).

13. The dermal filler according to claim 12, wherein the one or more peptides are selected from the group consisting of KGYNYSYKSEMKVRPA (SEQ ID NO: 1), GGWTVFQRRVDGSVDFYRK (SEQ ID NO: 2), KGYNYSYKVSEMKFQRRVDGSVDFYRK (SEQ ID NO: 3), KGYKYSYKVSEMKVRPAK (SEQ ID NO: 4), GGWTVFQRRMDGSVDFYRK (SEQ ID NO: 5), KGYKYSYKGGWTVFQRRMDGSVDFYRK (SEQ ID NO: 6), KGYKYSYKVSEMKFQRRMDGSVDFYRK (SEQ ID NO: 7), and KGYKYSYKGGWTVFQRRMDGSVDFYR (SEQ ID NO: 8.

14. A method for treating damaged dermal connective tissue, comprising introducing into the damaged dermal connective tissue a pharmaceutical composition according to claim 1.

15. The method according to claim 14 wherein the pharmaceutical composition is administered by injection.

16. An isolated peptide consisting of the sequence KGYKYSYKVSEMKVRPAK (SEQ ID NO: 4).

\* \* \* \* \*